United States Patent [19]

Bender et al.

[11] 4,153,706

[45] May 8, 1979

[54] 6-HYDROXY-5,6-PHENYL-2,3,5,6-TETRAHYDROIMIDAZO[2,1-b]THIAZOLES

[75] Inventors: Paul E. Bender, Cherry Hill, N.J.; David T. Hill, North Wales, Pa.

[73] Assignee: SmithKline Corporation, Philadelphia, Pa.

[21] Appl. No.: 876,952

[22] Filed: Feb. 13, 1978

[51] Int. Cl.$^2$ .............................................. C07D 277/60
[52] U.S. Cl. ............................... 424/270; 260/306.7 T
[58] Field of Search .................. 260/306.7 T; 424/270

[56] References Cited

U.S. PATENT DOCUMENTS

| 3,274,209 | 9/1966 | Raeymaekers et al. | 260/306.7 |
|---|---|---|---|
| 3,455,924 | 7/1969 | Lednicer et al. | 260/256.4 |
| 4,064,260 | 12/1977 | Cherkofsky | 260/306.7 T |

FOREIGN PATENT DOCUMENTS

| 852259 | 9/1977 | Belgium. |
|---|---|---|
| 3364 | 11/1977 | Syria. |

OTHER PUBLICATIONS

Derwent, Abstract 64982y.
Derwent, Abstract 40,535 (Rumanian Patent 226622.
Chemical Abstracts 72 12645p (1970), Abstract of Mazur et al., Khim–Farm. Zh. 3(8) 11–15(1969).

*Primary Examiner*—Nicholas S. Rizzo
*Attorney, Agent, or Firm*—Joan S. Keps; Richard D. Foggio; William H. Edgerton

[57] ABSTRACT

The compounds are 6-hydroxy-5,6-substituted-phenyl-2,3,5,6-tetrahydroimidazo[2,1-b]thiazoles which have antiarthritic activity and are useful as intermediates for preparing 2,3-dihydroimidazo[2,1-b]thiazole antiarthritic compounds. A particular compound of this invention is 5,6-bis-(p-fluorophenyl)-6-hydroxy-2,3,5,6-tetrahydroimidazo[2,1-b]thiazole.

8 Claims, No Drawings

6-HYDROXY-5,6-PHENYL-2,3,5,6-TETRAHYDROIMIDAZO[2,1-b]THIAZOLES

This invention relates to new 6-hydroxy-2,3,5,6-tetrahydroimidazo[2,1-b]thiazoles having, in the 5 and 6 positions, p-substituted phenyl groups, the phenyl in the 6-position being substituted by an electron withdrawing group. These compounds have antiarthritic activity and are particularly of use in the treatment of rheumatoid arthritis. Also, these compounds are useful as intermediates for preparing the corresponding 5,6-substituted phenyl-2,3-dihydroimidazo[2,1-b]thiazole compounds which have antiarthritic activity.

The compounds of this invention are represented by the following formula:

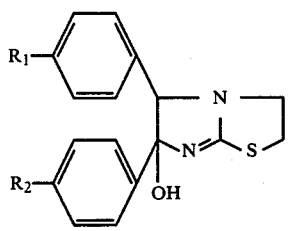

FORMULA I in which $R_1$ is lower alkoxy, lower alkylthio, fluoro, chloro, bromo or trifluoromethyl and $R_2$ is an electron withdrawing group, in particular, fluoro, chloro, bromo or trifluoromethyl.

Particular compounds of this invention are the compounds of Formula I in which $R_1$ and $R_2$ are both fluoro or both bromo, said compounds being 5,6-bis(p-fluorophenyl)-6-hydroxy-2,3,5,6-tetrahydroimidazo[2,1-b]thiazole and 5,6-bis(p-bromophenyl)-6-hydroxy-2,3,5,6-tetrahydroimidazo[2,1-b]thiazole.

The compounds of this invention are prepared by the following procedures:

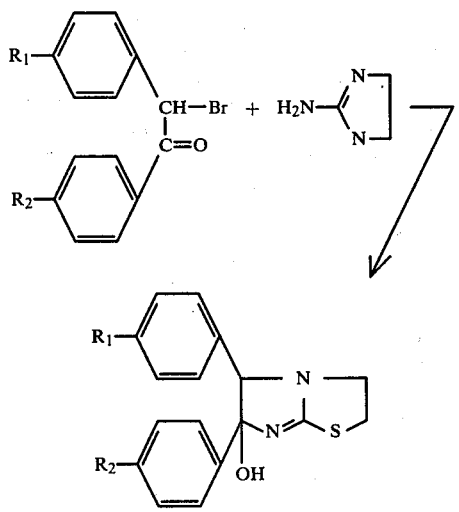

According to the above procedure, an α-bromodesoxybenzoin is reacted with 2-amino-4,5-dihydrothiazole. The reaction is carried out at room temperature in the presence of an added base, such as potassium carbonate or triethylamine, in acetonitrile. Alternatively, other anhydrous organic solvents may be used in place of acetonitrile.

The α-bromodesoxybenzoin starting materials in the process described above are known to the art or are prepared by bromination of the desoxybenzoins. The desoxybenzoins are known to the art or are prepared, for example, by the Friedel-Crafts reaction of a substituted phenylacetyl chloride with a substituted benzene in the presence of a Lewis acid. Desoxybenzoins may also be prepared by the Curtius rearrangement that is by isocyanate hydrolysis of 2,3-diarylacrylic acids. Diarylacrylic acids are known to the art or may be prepared by Perkin condensation of a substituted benzaldehyde with a substituted phenyl acetic acid in the presence of a base. Desoxybenzoins may also be prepared by reacting a substituted benzonitrile with a substituted benzyl magnesium chloride or by reduction of benzoins, for example using tin and hydrochloric acid. Methods for the preparation of benzoins and desoxybenzoins are well known to the art, see for example "Organic Reactions", Vol. IV, Chapter 5 "The Synthesis of Benzoins" (John Wiley & Sons, Inc., New York, 1948).

The compounds of Formula I may exist as cis and trans isomers in d, l and racemic forms and the formulas presented herein are intended to include all the isomers, both the separated isomers and mixtures thereof.

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily doses of about 6.5–50 mg./kg. orally. In this test procedure, adjuvant arthritis in rats is produced by a single intradermal injection of 0.75 mg. of Mycobacterium butyricum suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to protect the animals against the development of both primary and secondary lesions of adjuvant arthritis.

In addition, compounds which have immunoregulatory activity provide benefit for treatment of rheumatoid arthritis. Stiller et al., Annals of Internal Medicine 82:405–410 (1975), Froland et al., Scandinavian J. Immunol. 3.223–228 (1974) and The Lancet, Jan. 11, 1975, page 111. It has been found that compounds of this invention, particularly compounds of Formula I in which $R_1$ and $R_2$ are both chloro, bromo and trifluoromethyl, demonstrate the ability to regulate cell-mediated immunity as shown in procedures such as the oxazolone-induced contact sensitivity test procedure in which mouse paw is measured. This procedure is described by Griswold et al., Cellular Immunology 11:198–204 (1974). In contrast to anti-inflammatory agents, such as indomethacin, and immunosuppressive agents, such as methotrexate and cyclophosphamide, both of which inhibit the oxazolone-induced response, compounds of this invention at doses of from about 50 mg./kg., orally, not only do not inhibit but enhance the oxazolone-induced response.

In addition to having utility, in rheumatoid arthritis, immunoregulatory agents have potential utility in other diseases where cell mediated immunity is compromised. Examples of such diseases are systemic lupus erythematosus and autoimmune thyroiditis (Stiller et al. cited hereabove). Also, diseases such as atopic dermatitis, recurrent aphthus ulceration, recurrent upper respiratory tract infections in children and flu, lung and breast cancer, transient granulocytopenia and allergic skin reactions have been successfully treated with levamisole which is an agent which restores impaired cell mediated immune responses [Symoens et al., *Journal of the Reticuloendothelial Society,* 21:175-221 (1977)].

Somes of the compounds of this invention, for example those compounds of Formula I in which $R_1$ and $R_2$ are both fluoro, demonstrate, principally, activity in the test for inhibition of adjuvant induced polyarthritis in rats. Other compounds of this invention, such as those of Formula I in which $R_1$ and $R_2$ are both chloro, bromo or trifluoromethyl demonstrate activity in both the adjuvant induced polyarthritis and the oxazolone test procedures. Although all of these compounds are useful in the treatment of arthritis, compounds having activity in both tests are particularly advantageous in treatment of arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 25 mg. to about 150 mg.

The method of producing antiarthritic activity by administering internally to an animal a compound of Formula I is also an object of this invention. The compound of Formula I is administered in an amount sufficient to produce antiarthritic activity. The route of administration may be orally or parenterally. The daily dosage regimen will be preferably from about 75 mg. to about 450 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The compounds of Formula I are also useful as intermediates for the preparation of 5,6-substituted phenyl-2,3-dihydroimidazo[2,1-b]thiazoles which have antiarthritic activity. These 2,3-dihydro compounds are prepared by treating the hydroxy compounds of Formula I with acid such as hydrochloric acid or by heating in a suitable solvent such as methanol, toluene or dimethylformamide.

The terms "lower alkyl" and "lower alkoxy" where used herein denote groups having preferably 1-4 carbon atoms.

The following examples are not limiting but are illustrative of the invention.

EXAMPLE 1

To a stirred mixture of 5.94 g. of powdered 2-amino-4,5-dihydrothiazole and 8.03 g. of powdered anhydrous potassium carbonate in 100 ml. of sieve dried acetonitrile was added 10.0 g. of p,p'-dichloro-α-bromodesoxybenzoin. After 24 hours, the suspension was filtered and the solid was mixed with water. The aqueous suspension was extracted three times with chloroform. The combined chloroform extracts were washed with water and dried over potassium carbonate. The solvent was evaporated, and the solid was triturated with hexane and recrystallized from methanolwater to give 5,6-bis(p-chlorophenyl)-6-hydroxy-2,3,5,6-tetrahydroimidazo[2,1-b]thiazole, m.p. 171°-172° C. (dec.)

EXAMPLE 2

A mixture of 300 g. (1.39 moles) of p-bromophenylacetic acid and 663.8 g. (5.58 moles) of thionyl chloride was refluxed under nitrogen for 1 hour. The excess thionyl chloride was removed in vacuo. A stirred mixture of this residue, 436.5 g. (2.78 moles) of bromobenzene (distilled) and one liter of sieve dried methylene chloride, under nitrogen atmosphere, was treated portionwise with 222.4 g. (1.67 moles) of aluminum chloride. The mixture was refluxed for 75 minutes, allowed to cool to room temperature and added slowly to aqueous hydrochloric acid. Additional methylene chloride was added, and the organic layer was washed with dilute aqueous sodium carbonate, twice with water, dried over potassium carbonate and evaporated in vacuo. The residue was recrystallized from methylene chloride-hexane to give p,p'-dibromodesoxybenzoin, m.p. 131°-137° C.

To 52.2 g. (0.147 mole) of p,p'-dibromodesoxybenzoin in 500 ml. of benzene was added 23.56 g. (0.147 mole) of bromine dropwise. The solution was stirred for 1 hour and evaporated in vacuo. The material was recrystallized from benzene-hexane to give α,p,p'-tribromodesoxybenzoin.

A mixture of 22.21 g. (0.0507 mole) of α,p,p'-tribromodesoxybenzoin, 10.36 g. (0.101 mole) of 2-amino-4,5-dihydrothiazole and 21.02 g. (0.152 mole) of potassium carbonate was stirred for 3 days in 150 ml. of acetonitrile under nitrogen at room temperature. Filtration of this mixture gave a solid which was washed with water and air dried to give 5,6-bis(p-bromophenyl)-6-hydroxy-2,3,5,6-tetrahydroimidazo[2,1-b]-thiazole. Thirty-seven percent of this solid was stirred in 100 ml. of methanol under an inert atmosphere and 8.9 g. of a 45.1% solution of methanolic hydrogen chloride was added dropwise. The solution was heated to reflux for 30 minutes and then evaporated in vacuo. The residual solid was dissolved in hot methanol, treated with charcoal, filtered, treated with water, adjusted to pH 11 with aqueous sodium hydroxide, chilled and filtered to give 5,6-bis(p-bromophenyl)-2,3-dihydroimidazo[2,1-b]thiazole, m.p. 208°–210° C.

Also, the 5,6-bis(p-bromophenyl)-6-hydroxy compound was prepared as follows:

To 100 ml. of sieve dried acetonitrile were added with stirring 15.0 g. of powdered α,p,p'-tribromodesoxybenzoin, 6.70 g. of powdered 2-amino-4,5-dihydrothiazole and 14.18 g. of powdered potassium carbonate. After stirring for 3 days, the suspension was filtered, the solid triturated with water and filtered. A solution of this solid in methylene chloride was dried over anhydrous potassium carbonate, treated with charcoal, and crystallized by addition of hexane. Recrystallization from methylene chloride-hexane gave 5,6-bis(p-bromophenyl)-6-hydroxy-2,3,5,6-tetrahydroimidazo[2,1-b]thiazole, m.p. 164°–166° C. (dec.)

EXAMPLE 3

11.2 Grams (0.07 mole) of bromine in benzene (65 ml.) was added dropwise to a benzene slurry (65 ml.) of 16.3 g. (0.07 mole) of p,p'-difluorodesoxybenzoin stirred at 0° C. The solvent was then removed at reduced pressure to give p,p'-difluoro-α-bromodesoxybenzoin.

A slurry of 14.3 g. (0.07 mole) of p,p'-difluoro-α-bromodesoxybenzoin, 11.2 g. (0.06 mole) of 2-amino-4,5-dihydrothiazole and 18.6 g. (0.12 mole) of sodium carbonate in acetonitrile (150 ml.) was stirred overnight at room temperature. The precipitate was removed by filtration and extracted with methylene chloride. The extract was then washed with water, dried over magnesium sulfate, filtered and the solvent removed at reduced pressure to give 5,6-bis(p-fluorophenyl)-6-hydroxy-2,3,5,6-tetrahydroimidazo[2,1-b]thiazole, m.p. 159°–160° C. This was then dissolved in ethanol and ethereal hydrogen chloride added. The solution was cooled and the resulting crystals removed to give 5,6-bis(p-fluorophenyl)-2,3-dihydroimidazo[2,1-b]thiazole hydrochloride, m.p. 280°–282° C.

Also, the 5,6-bis(p-fluorophenyl)-6-hydroxy compound was prepared as follows:

To a stirred mixture of 5.75 g. of powdered 2-amino-4,5-dihydrothiazole and 7.74 g. of powdered anhydrous potassium carbonate in 90 ml. of sieve dried acetonitrile was added 8.75 g. of p,p'-difluoro-α-bromodesoxybenzoin in 10 ml. of dry acetonitrile. After 24 hours, the suspension was filtered and the solid obtained was triturated with water, filtered, and dried in vacuo. Recrystallization from methanol-water gave 4.3 g. of 5,6-bis(p-fluorophenyl)-6-hydroxy-2,3,5,6-tetrahydroimidazo[2,1-b]thiazole, m.p. 177°–179.5° C. (dec.)

EXAMPLE 4

A solution of 15 g. (0.042 mole) of p,p-bis-(trifluoromethyl)-α-phenylcinnamic acid and thionyl chloride (60 ml.) in benzene (100 ml.) was refluxed for 2 hours. The volatile materials were removed at reduced pressure and the residue dissolved in acetone (50 ml.). The acetone solution was added dropwise, with stirring, to a solution of 2.7 g. (0.042 mole) of sodium azide in water (20 ml.) at 10°–15° C. After one hour, the cold solution was extracted with benzene, the benzene extract washed with water and dried over magnesium sulfate. The mixture was filtered and the acid azide solution refluxed for 30 minutes. The benzene was removed at reduced pressure and the residual acid isocyanate treated with 75 ml. of a 2:1 acetic acid-water solution at 65° C. for one hour. The resulting precipitate was collected, washed with water and recrystallized from ethanol to give p,p'-di(trifluoromethyl)desoxybenzoin, m.p. 113°–115° C.

A solution of 6.2 g. (0.039 mole) of bromine in benzene (20 ml.) was added dropwise to 8.3 g. (0.025 mole) of p,p'-di(trifluoromethyl)desoxybenzoin in benzene (100 ml.). An infra red lamp was used initially to induce bromination. After 20 minutes, the solvent was removed at reduced pressure to give p,p'-di(trifluoromethyl)-α-bromodesoxybenzoin, m.p. 59°–60° C. (from hexane).

The bromodesoxybenzoin was dissolved in acetonitrile (100 ml.), 2.6 g. (0.025 mole) of 2-amino-4,5-dihydrothiazole and 7.0 g. (0.05 mole) of potassium carbonate was added and the mixture was stirred at room temperature for 60 hours. The solvent was removed at reduced pressure and the residue dissolved in chloroform (300 ml.). The chloroform solution was washed with water, dried over potassium carbonate and the solvent removed at reduced pressure to give 6-hydroxy-5,6-bis(p-trifluoromethylphenyl)-2,3,5,6-tetrahydroimidazole[2,1-b]thiazole, m.p. 175°–177° C.

A solution of 2.9 g. (6.7 mmoles) of 6-hydroxy-5,6-bis(p-trifluoromethylphenyl)-2,3,5,6-tetrahydroimidazo[2,1-b]thiazole in toluene (200 ml.) was refluxed with continuous azeotropic distillation of the resulting water. The solvent was removed at reduced pressure and the residue dissolved in ethanol and treated with 48% aqueous hydrobromic acid. The solution was evaporated to dryness and treated with 40 ml. of hot benzene. Filtration of the solid and drying gave 5,6-bis(4-trifluoromethylphenyl)-2,3-dihydroimidazo[2,1-b]thiazole hydrobromide, m.p. 314°–315° C.

EXAMPLE 5

A stirred suspension of 1.7 g. (0.012 mole) of anhydrous potassium carbonate and 1.26 g. (0.012 mole) of 2-amino-4,5-dihydrothiazole in acetonitrile was treated with 2.95 g. (0.0062 mole) of α-bromo-p-fluoro-p'-methoxydesoxybenzoin at 25° C. After 24 hours, the suspension was filtered, the filter cake was triturated in water, and this suspension extracted three times with methylene chloride. The combined extracts were washed with water, and hexane added to the organic phase to precipitate a solid. This was filtered and recrystallized from methanol-water to give 6-(p-fluorophenyl)-6-hydroxy-5-(p-methoxyphenyl)-2,3,5,6-tetrahydroimidazo[2,1-b]thiazole, m.p. 150.5°–151° C.

EXAMPLE 6

A mixture of p-fluorophenylacetic acid (25 g., 0.16 mole), p-methylthiobenzaldehyde (24.4 g., 0.16 mole), sodium methoxide (9.0 g., 0.17 mole) and acetic anhydride was refluxed for 20 hours. After cooling, water (500 ml.) was added and the mixture was cooled further in an ice bath. The resulting crystals were removed by filtration, washed with water, air dried and recrystallized from ethanol to give 2-(p-fluorophenyl)-3-(p-methylthiophenyl)acrylic acid, m.p. 167°–169° C.

2-(p-Fluorophenyl)-3-(p-methylthiophenyl)acrylic acid (28.8 g., 0.1 mole) was covered with thionyl chloride (60 ml.), refluxed for 90 minutes and the volatile material removed at reduced pressure. The residue was dissolved in acetone (200 ml.), filtered and added dropwise to an aqueous solution of sodium azide (7.2 g., 0.11 mole; 50 ml. water) kept at 0° C. The mixture was allowed to come to room temperature, water was added (400 ml.) and the mixture extracted with toluene. The extracts were washed with water and saturated brine, then dried over magnesium sulfate, filtered and allowed to stir overnight. The mixture was then refluxed for 90 minutes and the solvent removed at reduced pressure. The residue was then added to a 2:1 acetic acid-water mixture (100 ml.) and refluxed for two hours. Water (100 ml.) was added, the mixture cooled and the resulting precipitate collected by filtration, washed with water and recrystallized from ethanol to give p-fluoro-p'-methylthiodesoxybenzoin, m.p. 136°–138° C.

A carbon tetrachloride solution (10 ml.) of bromine (8.8 g., 55 mmole) was added dropwise to a carbon tetrachloride solution (150 ml.) of p-fluoro-p'-methylthiobenzoin (14.4 g., 55 mmole) kept at 0° C. After 45 minutes, the solvent was removed at reduced pressure to give, as the residue, α-bromo-p-fluoro-p'-methylthiodesoxybenzoin.

The above prepared α-bromodesoxybenzoin is dissolved in acetonitrile (100 ml.) and 2-amino-4,5-dihydrothiazole (5.2 g., 56 mmole) and potassium carbonate (7.8 g., 56 mmole) are added. After three days at room temperature, the mixture is filtered and the solid obtained is washed with water, dried and dissolved in chloroform. Hexane is added and the resulting solid is removed by filtration and dried to give 6-(p-fluorophenyl)-6-hydroxy-5-(p-methylthiophenyl)-2,3,5,6-tetrahydroimidazo[2,1-b]thiazole.

EXAMPLE 7

In the procedure of Example 2, using as a starting material in place of bromobenzene the following:
fluorobenzene
chlorobenzene
the products are:
5-(p-bromophenyl)-6-(p-fluorophenyl)-6-hydroxy-2,3,5,6-tetrahydroimidazo[2,1-b]thiazole
5-(p-bromophenyl)-6-(p-chlorophenyl)-6-hydroxy-2,3,5,6-tetrahydroimidazo[2,1-b]thiazole

EXAMPLE 8

| Ingredients | Amounts |
| --- | --- |
| 5,6-bis(p-bromophenyl)-6-hydroxy-2,3,5,6-tetrahydroimidazo[2,1-b]-thiazole | 50 mg. |
| magnesium stearate | 5 mg. |
| lactose | 100 mg. |

The above ingredients are screened, mixed and filled into a hard gelatin capsule.

EXAMPLE 9

| Ingredients | Amounts |
| --- | --- |
| 5,6-bis(p-fluorophenyl)-6-hydroxy-2,3,5,6-tetrahydroimidazo[2,1-b]-thiazole | 100 mg. |
| calcium sulfate dihydrate | 150 mg. |
| sucrose | 20 mg. |
| starch | 10 mg. |
| talc | 5 mg. |
| stearic acid | 3 mg. |

The sucrose, calcium sulfate dihydrate and 5,6-bis(p-fluorophenyl)-6-hydroxy-2,3,5,6-tetrahydroimidazo[2,1-b]thiazole are mixed and granulated with 10% gelatin solution. The wet granules are screened, dried, mixed with the starch, talc and stearic acid, screened and compressed into a tablet.

Similarly, the other compounds of Formula I may be formulated into pharmaceutical compositions by the procedures of Examples 8 and 9.

These pharmaceutical compositions are administered orally to a subject in need of antiarthritic activity within the dose ranges given hereabove.

What is claimed is:

1. A compound of the formula:

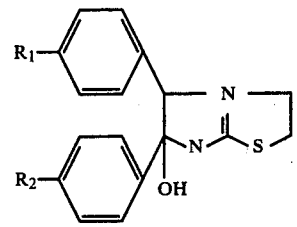

in which $R_1$ is lower alkoxy, lower alkylthio, fluoro, chloro, bromo or trifluoromethyl; and $R_2$ is fluoro, chloro, bromo or trifluoromethyl.

2. A compound of claim 1, said compound being 5,6-bis(p-fluorophenyl)-6-hydroxy-2,3,5,6-tetrahydroimidazo[2,1-b]thiazole.

3. A compound of claim 1, said compound being 5,6-bis(p-bromophenyl)-6-hydroxy-2,3,5,6-tetrahydroimidazo[2,1-b]thiazole.

4. A compound of claim 1, said compound being 5,6-bis(p-chlorophenyl)-6-hydroxy-2,3,5,6-tetrahydroimidazo[2,1-b]thiazole.

5. A compound of claim 1, said compound being 6-hydroxy-5,6-bis(p-trifluoromethylphenyl)-2,3,5,6-tetrahydroimidazo[2,1-b]thiazole.

6. A compound of claim 1, said compound being 6-(p-fluorophenyl)-6-hydroxy-5-(p-methoxyphenyl)-2,3,5,6-tetrahydroimidazo[2,1-b]thiazole.

7. A pharmaceutical composition having antiarthritic activity, in dosage unit form, comprising a pharmaceutical carrier and a compound of claim 1.

8. A method of producing antiarthritic activity which comprises administering internally to an animal a compound of claim 1.

* * * * *